(12) United States Patent
Platte et al.

(10) Patent No.: US 7,256,365 B2
(45) Date of Patent: Aug. 14, 2007

(54) ELECTRODE HOLDER WITH INTEGRATED ULTRASOUND SENSOR

(75) Inventors: Michael Platte, Wuppertal (DE); Heinz-Ullrich Mueller, Michelstadt (DE); Michael Lach, Erkrath (DE); Volker Arndt, Erbach (DE)

(73) Assignee: Bosch Rexroth AG, Stuttgart (DE)

( * ) Notice: Subject to any disclaimer, the term of this patent is extended or adjusted under 35 U.S.C. 154(b) by 24 days.

(21) Appl. No.: 10/805,765

(22) Filed: Mar. 22, 2004

(65) Prior Publication Data

US 2004/0206728 A1 Oct. 21, 2004

(30) Foreign Application Priority Data

Mar. 25, 2003 (DE) .................. 103 13 288

(51) Int. Cl.
*B23K 11/25* (2006.01)
*B23K 11/31* (2006.01)

(52) U.S. Cl. ..................... 219/109; 219/119

(58) Field of Classification Search ........... 219/109, 219/119, 84, 86.25, 158, 91.1, 706
See application file for complete search history.

(56) References Cited

U.S. PATENT DOCUMENTS

| 3,384,733 A | * | 5/1968 | Burbank et al. ............ 219/109 |
| 3,739,628 A | * | 6/1973 | Saglio ........................ 73/627 |
| 4,480,475 A | * | 11/1984 | Tsao et al. .................. 73/610 |
| 4,542,277 A | * | 9/1985 | Cecil ......................... 219/109 |
| 4,711,984 A | * | 12/1987 | Bilge et al. ................ 219/110 |
| 5,920,014 A | * | 7/1999 | Waschkies .................. 73/597 |
| 6,297,467 B1 | * | 10/2001 | Maev et al. ............... 219/109 |
| 6,414,260 B1 | * | 7/2002 | Vogt .......................... 219/109 |
| 6,515,251 B1 | * | 2/2003 | Wind ........................ 219/86.1 |
| 2004/0079156 A1 | * | 4/2004 | Arndt et al. ................ 73/588 |

FOREIGN PATENT DOCUMENTS

| DE | 199 37 479 A1 | 3/2001 |
| WO | 94/03799 | 2/1994 |

\* cited by examiner

*Primary Examiner*—Kevin Kerns
*Assistant Examiner*—Michael Aboagye
(74) *Attorney, Agent, or Firm*—Michael J. Striker (57) ABSTRACT

A connecting element for connecting and/or fixing an electrode with an electrode arm of a welding apparatus has a base body; and a sensor selected from the group consisting of a sensor for introducing ultrasound waves into an electrode, a sensor for receiving ultrasound waves and both.

20 Claims, 7 Drawing Sheets

ELECTRODE HOLDER WITH INTEGRATED ULTRASOUND SENSOR

CROSS-REFERENCE

The invention described and claimed hereinbelow is also described in DE 103 13 288.0, filed Mar. 25, 2003. This German Patent Application, whose subject matter is incorporated hem by reference, provides the basis for a claim of priority of invention under 35 U.S.C. 119 (a)–(d).

BACKGROUND OF THE INVENTION

The present invention relates to an arrangement of a sensor, in particular an ultrasound sensor for process control of a welding process.

More particularly, the present invention relates to a connecting element for connection of an electrode with an electrode arm of a holder device for holding welding electrodes.

The present invention also relates to a holding device, in particular of a welding apparatus for resistance welding.

For process control of a welding process, in particular for process control of a welding process with resistance point welding, it has been found very efficient to treat the region to be welded with ultrasound during the welding process and to use the ultrasound absorption rate or the residual sound level which remains after the ultrasonic treatment as control variables for the process control. The basic physical process for this purpose is disclosed in the international patent application WO 94/03799. As described there, shear or transverse waves are passed through the welding region or the joining parts during the welding process. For this purpose on the electrode shaft of the first of both oppositely located welding electrodes, an ultrasound transmitter is mounted for producing ultrasound waves and for directing these sound waves in the electrode shaft in direction to the welding region. On the electrode shaft of the second welding electrode which is located opposite to the first welding electrode, a receiver is arranged for receiving the ultrasound which passes through the welding region. The generated ultrasound signal passes from the ultrasound transmitter as structure-born sound through the electrode shaft of the first electrode to a welding product, for example two metal sheets to be welded with one another, and passes through it, so as to finally reach the ultrasound receiver through the shaft of the second electrode. The received sound level is converted there into an electrical signal, and supplied as control variables to the control device as input variables, for controlling the value of the welding current, with which the welding electrodes are provided.

It has been determined that the use of transverse ultrasound waves or ultrasound waves with high transverse portion is especially well suitable for evaluation of the welding condition and for control of the welding process. Transverse ultrasound waves during passage through a fluid lens which is produced during welding as a welding lens of the molten metal, are evaporated especially intensely. Thereby, based on the measurements of the evaporation of the transmitted ultrasound intensity, a reliable expression of the formation and size of the welding lens is possible, which can be used as control variables in for a control process for controlling the welding process.

An important criterium for a good performance of the method, in addition to the use of suitable ultrasound waves, is in particular the type of the introduction of the sound into the electrodes, the sound propagation in the electrodes, and finally the reception of the sound. In the international patent document WO 94/03799 the ultrasound transmitter and the ultrasound receiver for this purpose are mounted on the electrode shafts of the electrodes or on the electrode holders. The ultrasound transmitter and receiver are here shear waves testing heads which have piezo elements. During excitation with an electrical voltage it carries out a shear movement, and vice versa during excitation with a shear movement it generates a receiving voltage.

For receiving a high radiation of the ultrasound waves in direction of the welding product as well also an oriented reception of the sound waves, it is proposed in the document WO 94/03799 to use attachment wedges under the transmitters and receivers. Thereby an orientation of the sound radiation is produced in direction of the central axis of the electrode.

The arrangement disclosed in the international patent document WO 94/03799 has however the disadvantage that the concept of arranging the ultrasound transmitter and the ultrasound receiver is expensive to develop and to realize. For each use, electrode holders or electrodes provided with transmitters or receivers must be manufactured.

German patent document DE 199 37 479 A1 discloses a sensor device, in which the sensor carrier has a receptacle for receiving the transmitter or receiver and thereby a direction-improved sound introduction or a direction-improved sound reception is possible. In the same way as above, each sensor carrier must be provided however with a transmitter and/or a receiver.

In order to make possible welding of a plurality of components with different shapes, conventionally a plurality of electrodes of different lengths, diameters and shapes as well as a plurality of different electrode holders are utilized. In order to realize the solution proposed in the German document DE 199 37 479 A1, it is necessary to provide a plurality of electrodes and/or electrode holders with transmitters and receivers and keep their supply. When the transmitter and receiver are applied in the electrode shaft, it is possible that the commercial electrode shafts which are producible as simple rotary parts in a cost favorable manner, can no longer be used. In case of a damage of the electrode shaft or of the sensor, in addition the whole unit including the electrode shaft together with the sensor must be exchanged.

In an unpublished German patent application of the applicant it is proposed to arrange the transmitter and receiver in a ring-shaped, longitudinally slotted clamping element, such that the clamping element can be fitted on the cylindrical electrode shaft of an electrode and fixed by clamping on the longitudinal slot on the electrode. In this way it is possible to exchange for example the electrodes, but to use the transmitter and receiver further by simply mounting them on a new electrode.

It has been however determined that mounting of a clamping element on the shaft of a welding electrode is often not possible due to narrow available space or the welding would be significantly hindered.

Figure 2:
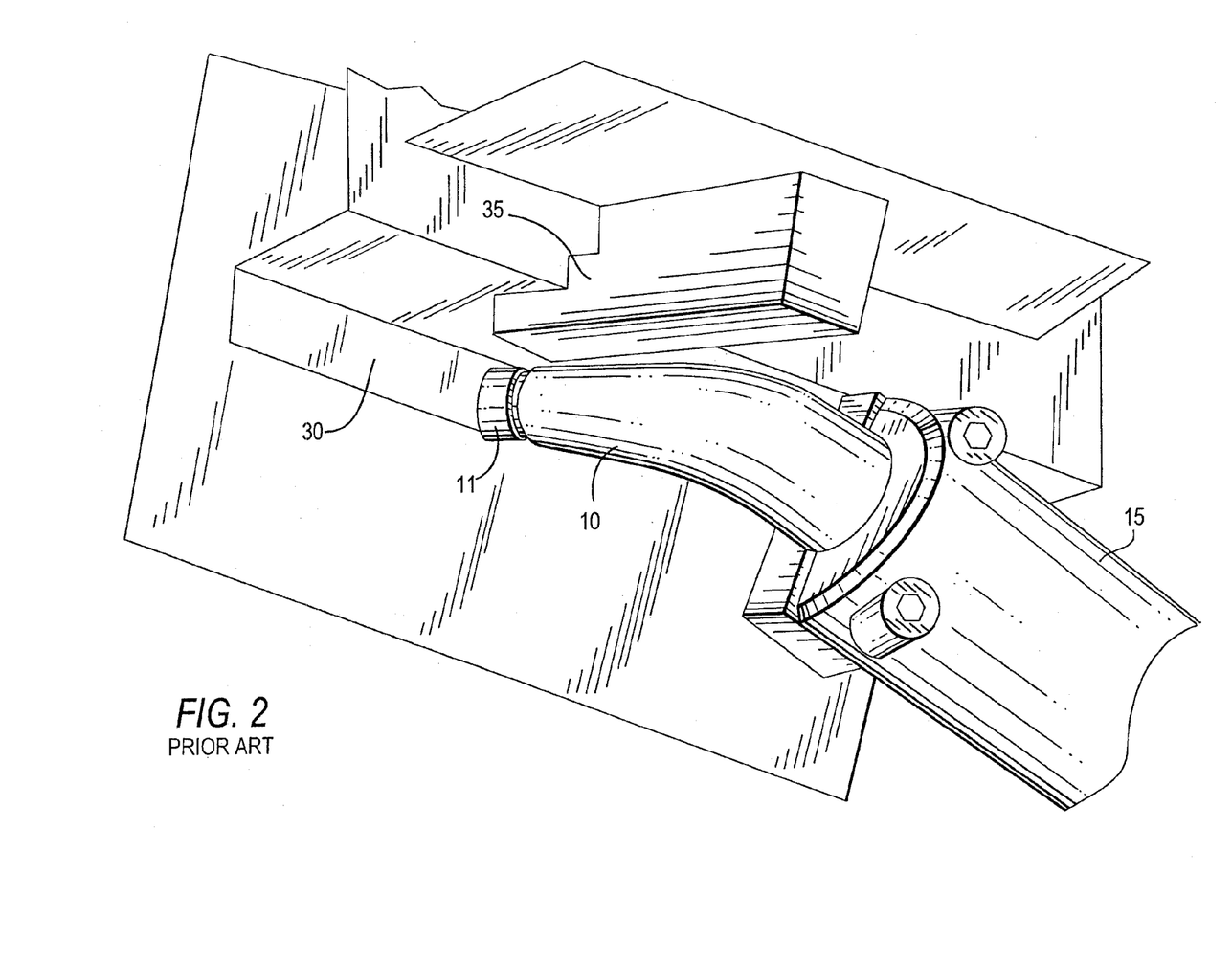
FIG. 2 is a view showing a component to be welded with a narrowed operational region.
Figure 3:
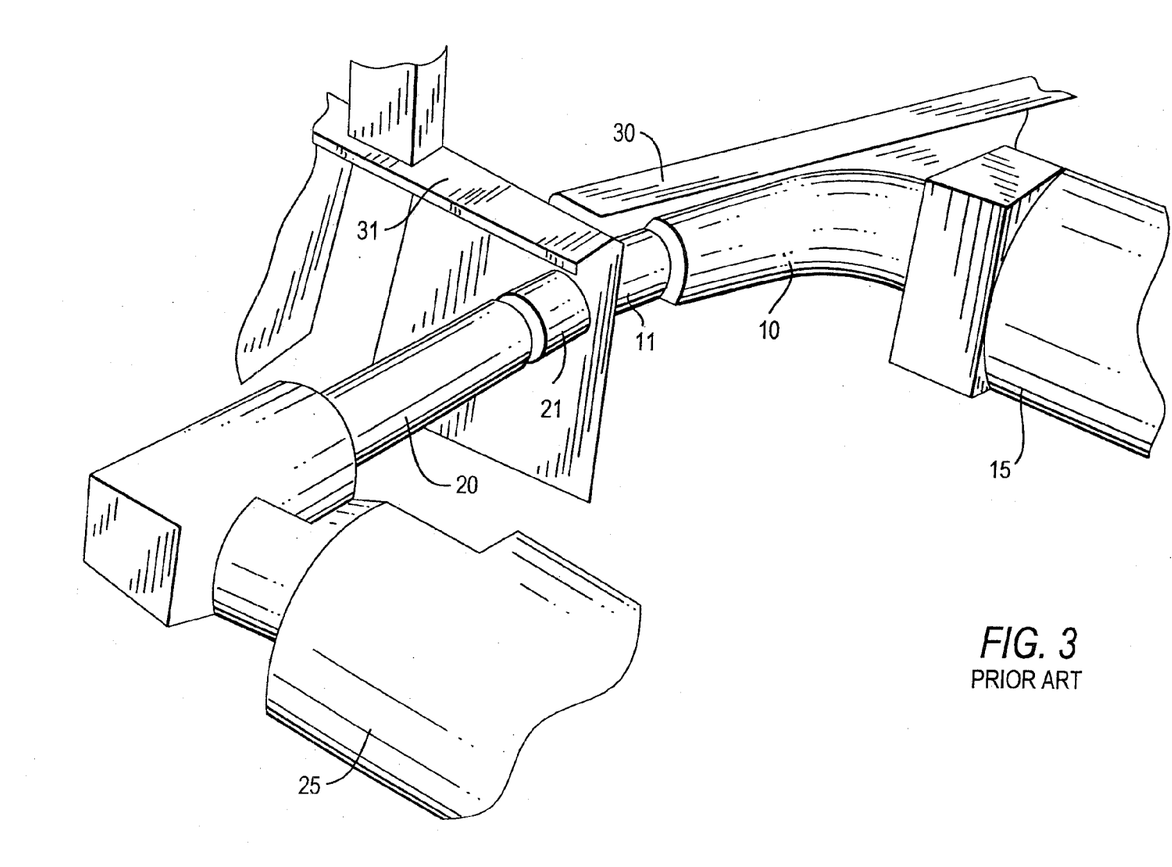
FIG. 3 is a view showing a further component to be welded with a narrowed operational region.

In FIGS. 2 and 3 welding situations are shown, in which the distance to one component to be welded, or to a clamping element which holds the component to be welded, is very small. The additional clamping element proposed in this unpublished patent application therefore can not be used.

SUMMARY OF THE INVENTION

Accordingly, it is an object of the present invention to provide a holding device for holding electrodes, in particular welding electrodes for resistance welding, with a sensor integrated in the holding device, in particular an ultrasound sensor, in which the disadvantages of the prior art are eliminated.

It is another object of the present invention to provide a holding device in which a sensor, in particular an ultrasound sensor is arranged on an electrode holder so that the electrodes can be easily exchangeable while the same sensor can be used repeatedly.

In particular, it is also an object of the present invention to provide the arrangement of the sensor such that it does not negatively affect the welding operation region.

Moreover, the device is designed so that the sensor can be mounted and dismounted with a low mounting expense. Furthermore, the device is designed so that advantageously the generated sound waves are supplied without significant losses in the electrode and from there in direction to the welding product or the joining parts, and can be received from the direction of the welding product.

In keeping with these objects and with others which will become apparent hereinafter, one feature of the present invention resides, briefly stated, in a connecting element for connecting and/or fixing an electrode with an electrode arm of a welding apparatus, comprising a base body; and a sensor selected from the group consisting of a sensor for introducing ultrasound waves into an electrode, a sensor for receiving ultrasound waves, and both.

The inventive connecting element for connecting and/or fixing an electrode with an electrode arm of a welding device, preferably a resistance welding device, includes, in addition to a base body, a sensor for introducing ultrasound waves into the electrode and/or for receiving ultrasound waves.

Preferably, the ultrasound waves are transverse ultrasound waves or ultrasound waves with a predominantly transverse component, in particular shear waves and/or torsion waves. The inventive connecting element therefore represents a further improvement of connecting elements which are known in the prior art, as used in the prior art for connection of an electrode with an electrode arm and/or for fixing the electrode, and extend the functionality of such a connecting element which is known from the prior art by space economical integration of an ultrasound sensor on or in the base body of the connecting element.

With the inventive arrangement of the sensor in or on the base body of the connecting element it is possible to introduce ultrasound waves through the connecting element into the electrode or the electrode shaft, or receive the ultrasound waves from the electrode or the electrode shaft via the coupling with the connecting element. The place consumption of the total device including an electrode arm, an electrode, a connecting element and a sensor, when compared with known arrangements of the prior art without sensors, is not increased or increased only insignificantly so as not to causes any negative limitations for the operational region. Also, with the use of an inventive connection element, conventional electrodes can be utilized in the electrode arm as before. No special adaptation of the utilized electrodes for receiving or holding the ultrasound sensor are needed, so that a high flexibility of the total welding device is obtained simultaneously with lower operational costs. In particular, with the use of different electrodes the same sensor can be used again, so that no cost-intense supply of a plurality of sensors is needed.

In addition to the arrangement for a sensor for introducing of ultrasound waves in the electrodes and/for receiving of ultrasound waves, preferable transversely ultrasound waves or ultrasound waves with predominantly transversely components, in particular shear waves and/or torsion waves, alternatively or also additionally other sensors can be arranged in the connecting element. However, it is especially advantageous to arrange an ultrasound sensor for introducing ultrasound waves in the electrode or at least in the electrode shaft in or on the connecting element, since the connecting element for fixing the electrode directly adjoins the electrode. Thereby a good transmission of the generated sound waves from the connecting element in the electrode is provided.

In the present invention the term "sensor" is used both to identify a transmitter and a receiver. The construction of a transmitter often corresponds to the construction of the receiver. The differences between them are often only in control or evaluating electronic circuits connected to them.

Also, in the present application the term "electrode" is utilized in the sense of an electrode shaft. It is however not necessary to provide the electrode shaft also with an electrode cap.

For evaluation of the welding condition it has been determined that it is especially advantageous to use the sensors which produce or receive the transverse ultrasound waves or ultrasound waves with predominantly transverse components, in particular shear waves and/or torsion waves. For example, sound waves with a frequency smaller than 1 MHz are generated. It is especially advantageous to use horizontally polarized transverse waves, since they have a little tendency for undesired mode conversion during reflection inside the sound-guiding electrode holder. The sensors which are used as ultrasound transmitters or ultrasound receivers are preferably so-called shear wave testing heads. They contain flat and mainly round piezo plates of several millimeters to several centimeters in diameter. In response to excitation with an electrical voltage, a shear movement is performed, or vice versa in the case of reception a received shear wave reacts to a reception voltage. Preferably, the sensor on its rear side has at least one sound-damping and/or reflecting layer to guarantee an oriented radiation of the sound waves. Also, with this sound-damping and/or reflecting layer, no foreign sound influence can penetrate into the sensor from outside and lead to a false sound signal. Furthermore, it is advantageous to provide between the piezo electric layer of the sensor and the connecting element, an electrically insulating, but sound-transmitting intermediate layer.

Preferably, the sensor for introducing ultrasound waves is arranged in the electrode and/or the sensor for receiving of ultrasound waves is arranged on the base body of the connecting element. The sensor can be glued or held in a form-locking manner. It is necessary to take care that the glueing or mounting provides a good transmission of the sound waves from the sensor to the connecting element. A glueing is preferably performed with high pressure, so that a small glue layer is obtained which preferably is significantly smaller than a wave length of the produced sound waves.

It is especially advantageous when the sensor is arranged in a recess of the base body of the connecting element. Often, for arrangement of the sensor one of the end sides is provided, preferably the end side of the connecting element which faces the electrode arm. With this arrangement on the end side facing the electrode arm, the radiation of sound waves in direction of the welding region is simultaneously guaranteed. Preferably, the sensor is arranged on the connecting element or in the connecting element so that the ultrasound waves are introduced into the electrodes substantially parallel to the longitudinal axis of the electrode or under an angle of smaller than 20° to the longitudinal axis of the electrode.

Preferably the connecting element is formed as a clamping element which is connectable with the electrode arm, preferably with a counter plate of the electrode arm, so that the electrode with the electrode arm is fixed in a clamping seat. The connecting element can be carried also as an intermediate piece which is connectable on one side with the electrode arm and on the other side with the electrode.

The connecting element can be composed as a material which has the same or similar acoustic properties as the material of the electrode. Thereby a good transmission of the sound waves from the connecting element to the electrode and vice versa is guaranteed. In particular, only a small reflection of the sound waves takes place during the transmission from the connecting element to the electrode and vice versa, as well as only a small mode conversion.

In a further aspect, the invention deals with a holding device for holding of electrodes, in particular welding electrodes for resistance welding wherein the holding device includes an electrode arm and a connecting element connected with the electrode arm and designed as specified herein above.

The holding device conventionally includes preferably two electrode arms each with a connecting element, wherein in one of the connecting elements a sensor for introducing ultrasound waves into one electrode is provided, and in the other connecting element a sensor for receiving ultrasound waves is provided.

In order to perform the welding process, the electrodes are positioned on opposite sides of the welding product or the joining parts.

In a preferable embodiment of the inventive holding device, the diameter of the electrode arm is greater than the diameter of the electrode and the electrode arm on an end side has an opening for receiving a portion of the electrode.

It is especially advantageous when the electrode arm has a counter plate which is formed for example as a collar-shaped extension of the electrode arm, and is connectable with the connecting element for clamping the electrode preferably by screwing. This provides a very compact construction of the inventive holding device.

In accordance with a further embodiment of the present invention, a cylinder-shaped sensor is utilized, and it is mounted in a bore of the electrode arm on the connecting element. Because of the shape of the sensor, a small material removal during its mounting is needed, whereby the mechanical stability of the electrode arm or connecting element is improved.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 4 is a view showing a prior art holding device for holding an electrode;

DESCRIPTION OF THE PREFERRED EMBODIMENTS

Figure 1:
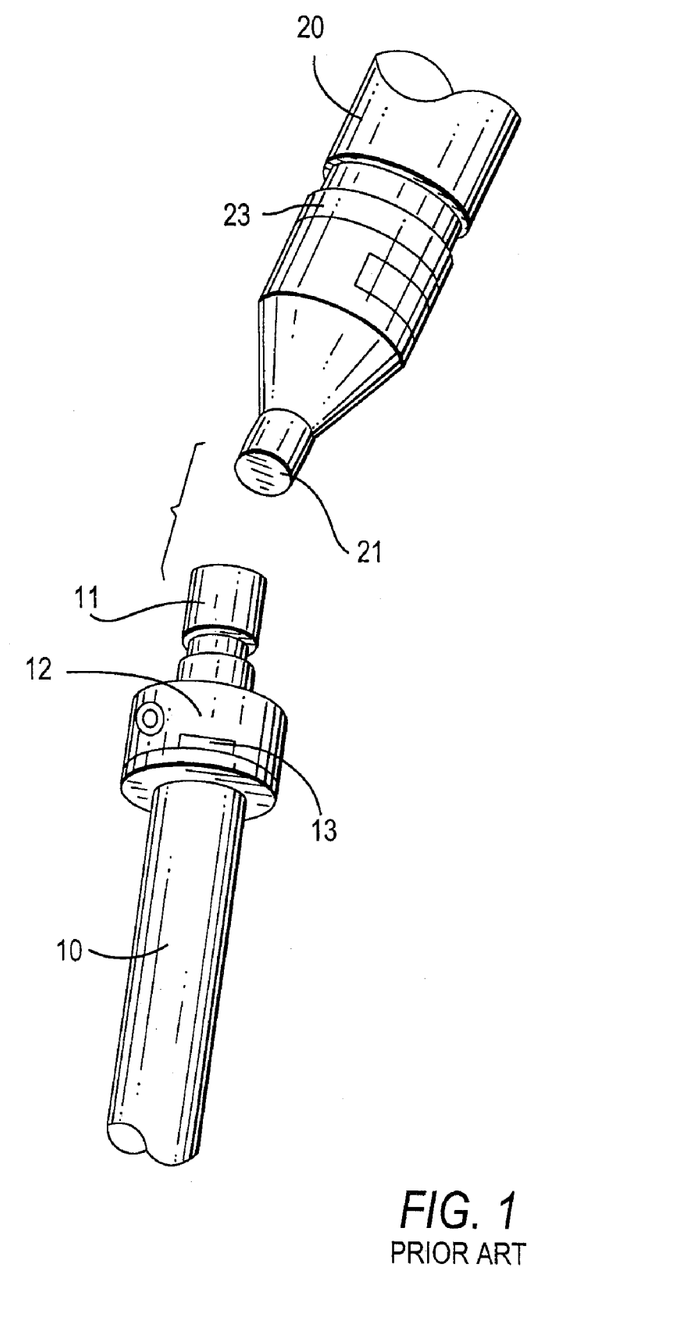
FIG. 1 is a view showing a prior art arrangement of an ultrasound sensor arranged in a ring-shaped attachment, wherein the attachment is fitted on an electrode shaft.

FIG. 1 shows an arrangement of an ultrasound sensor which is known from the prior art. The ultrasound sensor 13 is integrated in a ring-shaped attachment element 12, and the attachment element 12 is fitted on the cylindrical electrode shaft of a first electrode 10 and clamped there. The attachment element 12 for this purpose is arranged preferably near an electrode cap 11 which is plugged on the electrode 10 so that the conduction path for the transmitted ultrasound waves to the joining parts can be maintained as short as possible.

The joining parts or components to be welded or the welding product is positioned in FIG. 1 between the electrode caps 11, 21 of the first electrode 10 and a second electrode 20. For receiving the ultrasound passing through the welding product, a further ultrasound sensor 23 which operates as a receiver is arranged on the second, cone-shaped electrode 20 on the cone bottom.

As can be clearly seen from FIG. 1, because of the arrangement of the ring-shaped attachment element 12, the space consumption for the first electrode 10 is considerably greater than without the arrangement of the ring-shaped attachment element.

When the welding of such components must be performed, which are different to access, for example because of undercuts or other component overhangs, then the situation arises that the ring-shaped attachment element 12 abuts against a part of the component to be welded and thereby a welding is not possible. The ring-shaped attachment element 12 must be first removed to make possible carrying out of a welding. This welding is performed however again without a process control on the basis of a measured sound absorption.

FIG. 2 shows such a welding apparatus with narrowed spaced conditions. In addition to an angle electrode 10 which has a shaft extending over a 90° arc, a clamping of the electrode 10 in electrode 15 represents a holding device. In the shown welding apparatus the electrode 10 with the electrode cap 11 abuts against an inner front end of a component 30 to be welded. The shown component 30 is an angle plate, which must be welded on its rear side with a flat plate. The angle plate 30 is fixed with a clamping element 35 for welding. As shown in FIG. 2, the distance between the electrode 10 and the clamping element 35 is so small that an additional arrangement of a ring-shaped attachment element as in FIG. 1 is no longer possible.

Also, the apparatus shown in FIG. 3 is a further welding apparatus for resistance welding of a component with narrowed space conditions. Here two angle plates 30 and 31 are shown, which are connected with one another at a right angle. The welding location at the side of the first angle plate 30 is difficult to access. Here also it is not possible to use the attachment element as in FIG. 1. In addition to the electrodes 10 and 20, in FIG. 1 both electrode arms 15 and 25 for holding of the electrodes can be also seen.

Figure 4A:
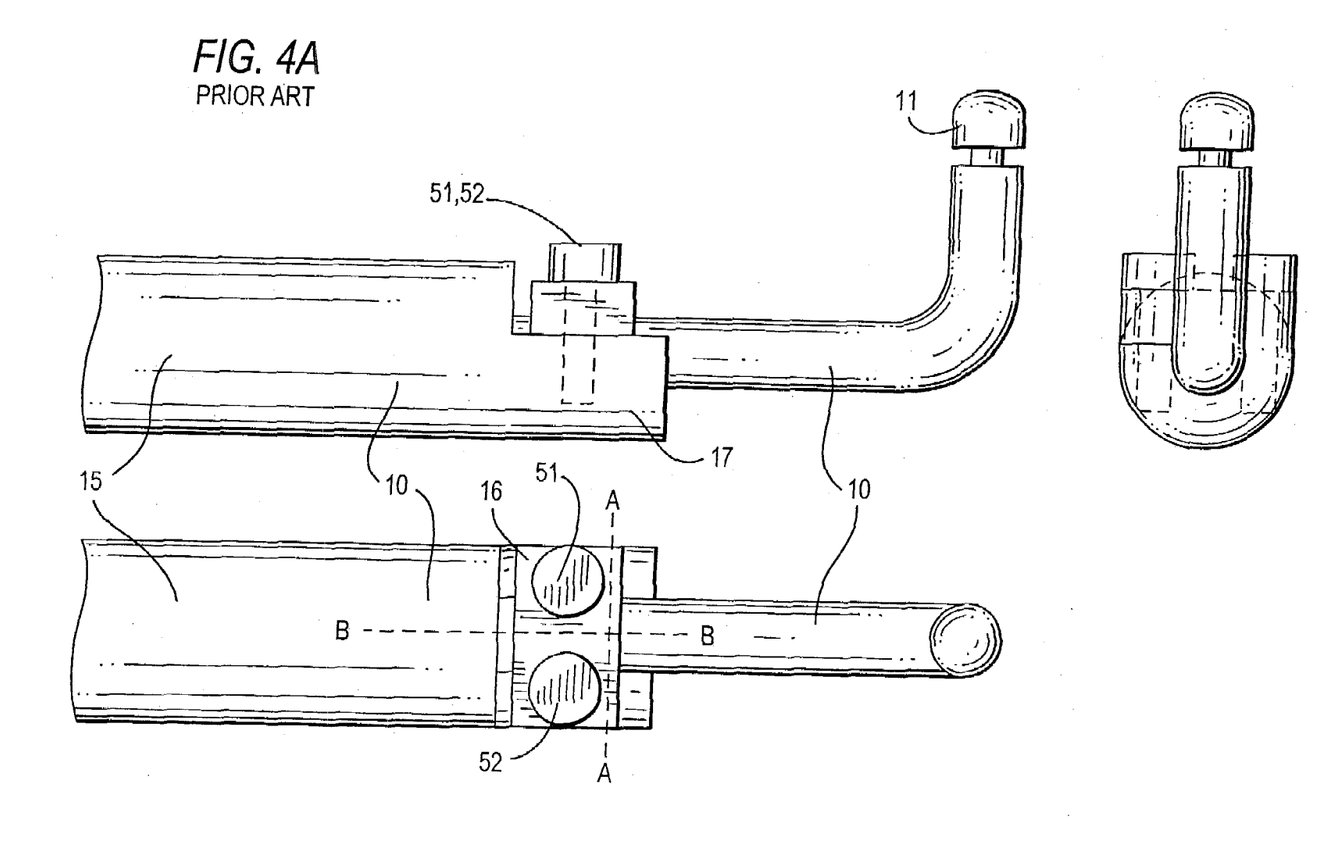
FIG. 4a is a view showing a prior art holding device for holding an electrode.

FIG. 4 shows a holding device for holding a welding electrode 10 which is known from the prior art. The holding device includes substantially a cylindrical electrode arm 15, with an opening on its front end side for receiving a portion of the electrode 10. The electrode 10 inserted in the opening is fixed by a clamping piece 16. For this purpose the clamping piece 16 with the counter plate 17, which is formed of one piece with the electrode arm 15 and extends outwardly beyond the front end side of the electrode arm 15, is screwed as identeified with 51, 52. Thereby a clamping of the electrode 10 is achieved. The clamping piece 16 further secures the electrode shaft 10 against turning and serves also for an electrical contacting between the electrode arm 15 and the electrode shaft of the electrode 10. On the front end of the electrode further an exchangeable electrode cap 11 is attached.

Figure 5:
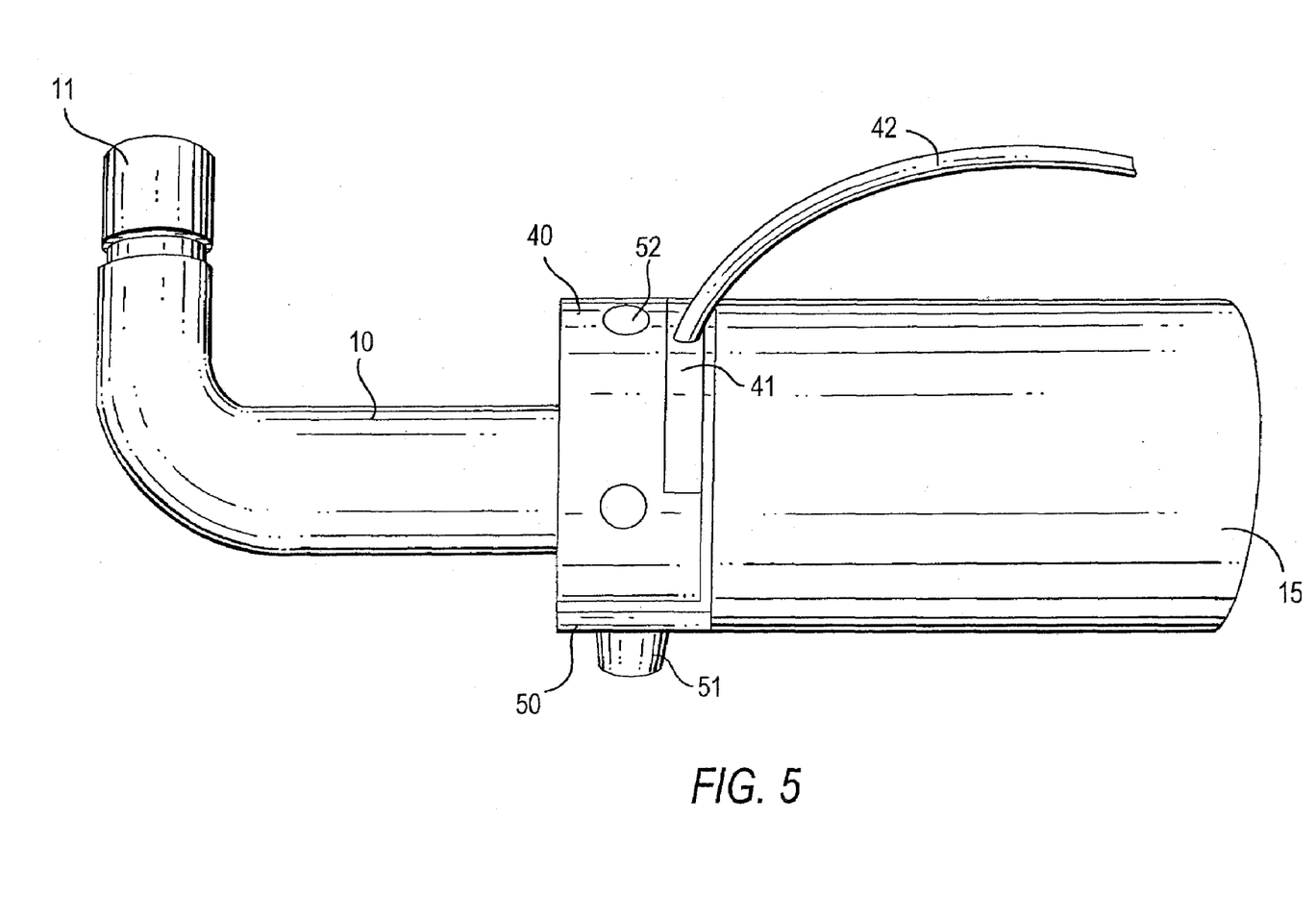
FIG. 5 is a view showing an inventive holding device with an ultrasound sensor integrated in a base body of a clamping element.
Figure 6:
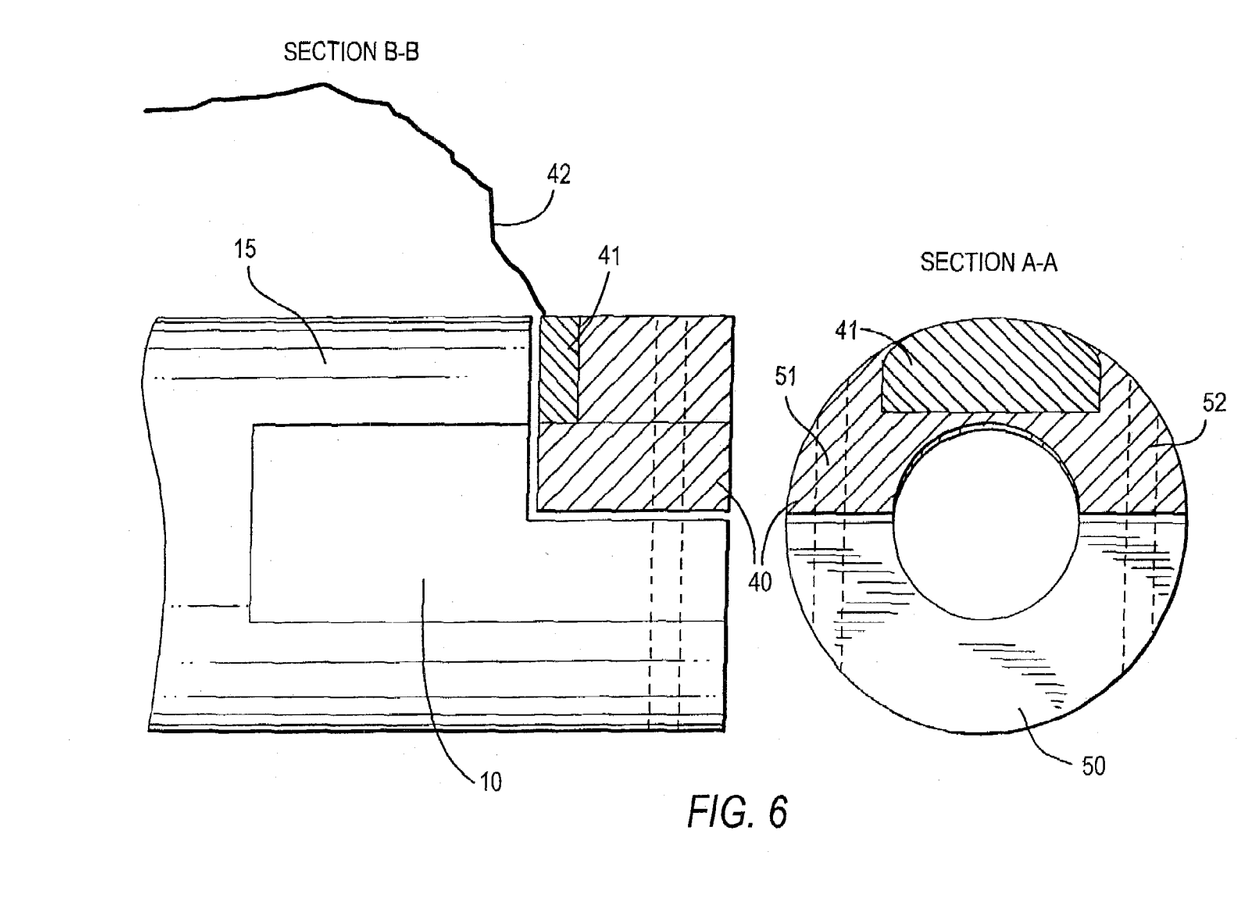
FIG. 6 is a view showing detail of the inventive holding device of FIG. 5.

FIG. 5 shows a holding device in accordance with the present invention. The construction of the holding device corresponds substantially to the construction shown in FIG. 4. Here in addition an ultrasound sensor 41 is integrated in a connecting element which is formed as a clamping piece 40. FIG. 6 shows a detail of the inventive holding device of FIG. 5, and in particular the inventive clamping piece 40.

The ultrasound sensor 41 is here introduced into a material recess of the base body of the clamping piece 40 at the end side of the clamping piece 40 which faces the electrode arm 15, and is glued there. Furthermore, a conductor cable 42 for transmitting electrical signals and/or the electrical supply voltage is shown in FIGS. 5 and 6. The clamping piece 40 has an inner contour corresponding to the outer contour of the electrode 10 or the electrode shaft. It is screwed by a screw connection which is formed here by two screws 51 and 52, with a counter plate 50. The counter plate 50 is formed as a collar-shaped extension of the electrode arm 15, of one piece with the electrode arm 15.

The outer contours of the base body of the clamping piece 40 as well as the ultrasound sensor 41 are advantageously formed in correspondence with the outer contour of the electrode arm, so that after assembly they produce a stepless outer contour.

Figure 7:
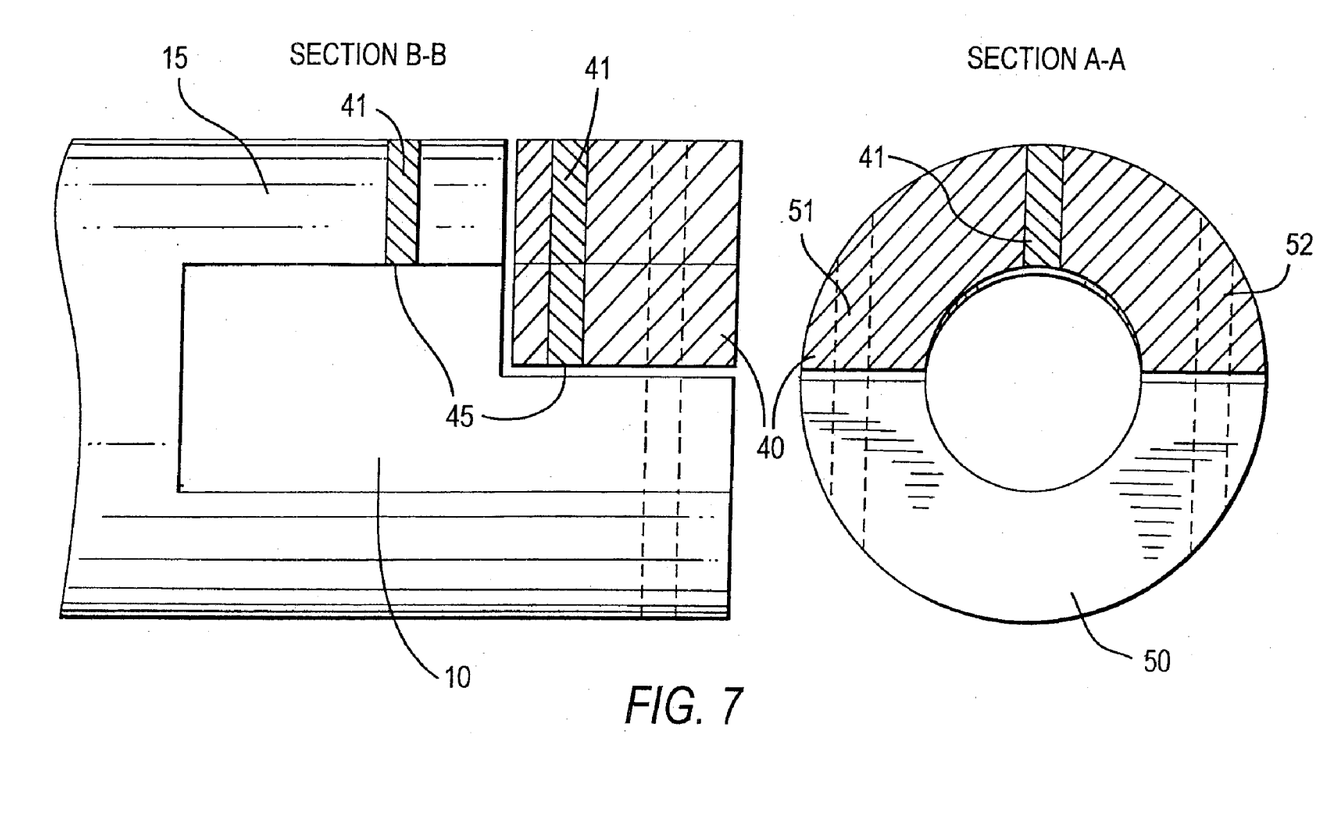
FIG. 7 is a view showing a detail of the inventive holding device with a cylinder-shaped sensor.

FIG. 7 shows a detail of the inventive holding device of FIG. 5, and in particular of the inventive clamping piece 40 with the cylindrical sensor 41. As a result of the clamping of the electrode 10 by the clamping piece 40, on the one hand directly a form-locking and a force-transmitting contact of the clamping piece 40 with the electrode 10 is provided.

Sound waves which are generated by the ultrasound sensor 41 are transmitted substantially without losses through the clamping piece 40 to the electrode shaft or the electrode 10 and from there they are further transmitted to the welding product.

The arrangement of the ultrasound sensor 41 on the end side of the clamping piece 40, which faces the electrode arm 15, is advantageously selected so that the ultrasound waves are introduced into the electrode at an angle of approximately 15°–20° to the longitudinal axis of the electrode.

Since the ultrasound sensor 41 is integrated in the clamping piece 40, the inventive arrangement requires a smaller component volume when compared with the arrangement shown in FIG. 1, in particular in the region of the electrodes 10 and 20. The electrodes 10 and 20 can be positioned, also with angled components or in narrowed space conditions, due holder construction or any further components, in an easy to handle manner on the component to be welded. This means that during the use of the inventive holding device, the locations which are difficult to access can be welded, and simultaneously a monitoring of the welding process based on the passage of ultrasound through the welding location can be performed.

It is also possible to exchange the electrodes which are used for welding, and to replace them by electrodes with another geometry and thereby to further use the same ultrasound sensor. In an opposite situation, in case of a defect of the ultrasound sensor, the electrode can be used further and the clamping piece with the ultrasound sensor applied on it can be exchanged.

A further advantage of the inventive arrangement of the ultrasound sensor on or in the connecting element resides in that the sensor is mounted outside of the working region, or in other words outside of such a region in which the disturbing edges occur, so that the sensor, in particular during the supply or removal of the electrode can abut against them and thereby can be damaged.

Also, the inventive sensor is characterized by a smaller dirtying when compared to a positioning of the sensor in the front region of the electrode. Also, no tear or a mechanical wear of the sensor or the holding device occurs during an exchange of an electrode caps.

It will be understood that each of the elements described above, or two or more together, may also find a useful application in other types of constructions differing from the types described above.

While the invention has been illustrated and described as embodied in electrode holder with integrated ultrasound sensor, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A connecting element for connecting and/or fixing an electrode with an electrode arm of a welding apparatus, comprising a base body; and a sensor disposed at an end side of said connecting element facing an electrode arm, wherein said sensor is selected from the group consisting of a sensor for introducing ultrasound waves into an electrode, a sensor for receiving ultrasound waves, and both, wherein the connecting element is formed as a clamping element which is connectable with the electrode arm so that it fixes the electrode in a clamping seat, wherein outer contours of the clamping element and sensor are formed to correspond with an outer contour of the electrode arm, so that after assembly, the clamping element, the sensor, and the electrode arm together produce a stepless outer contour.

2. A connecting element as defined in claim 1, wherein said sensor is a sensor for introducing and/or receiving of ultrasound waves selected from the group consisting of transverse ultrasound waves and ultrasound waves with predominantly transverse components.

3. A connecting element as defined in claim 1, wherein said sensor is a sensor for introducing and/or receiving of ultrasound waves selected from the group consisting of shear waves, torsion waves, and both.

4. A connecting element as defined in claim 1, wherein said sensor is arranged on said base body.

5. A connecting element as defined in claim 1, wherein said base body has a recess, said sensor being arranged in said recess of said base body.

6. A connecting element as defined in claim 1, wherein said clamping element has an inner contour which corresponds to an outer contour of the electrode; and further comprising screw means for connecting the clamping element with a counter plate which is formed as a collar-shaped extension of said electrode arm.

7. A connecting element as defined in claim 6, wherein said counter plate is formed of one piece with said electrode arm.

8. A connecting element as defined in claim 1, wherein the connecting element is composed of a material which has same or substantially similar acoustic properties as a material of the electrode.

9. A connecting element as defined in claim 1, wherein said sensor includes a piezo element.

10. A connecting element as defined in claim 1, wherein said sensor is arranged so that the ultrasound waves are introduced into the electrode in an orientation selected from the group consisting of an orientation substantially parallel to a longitudinal axis of the electrode and an angle of smaller than 90° to a longitudinal axis of the electrode.

11. A connecting element as defined in claim 1, wherein said sensor is formed so that the ultrasound waves have a frequency smaller than 1 Mhz.

12. A connecting element as defined in claim 1, wherein said sensor is provided with a sound-influencing layer.

13. A connecting element as defined in claim 12, wherein said sound influencing layer is a layer selected from the group consisting of a sound-damping layer, a reflecting layer, and both.

14. A connecting element device as defined in claim 1, wherein said connecting element has an opening, said sensor being cylinder-shaped and mounted in said opening of said connecting element, and also being in contact with an end side of said electrode.

15. A holding device for holding electrodes for resistance welding, comprising an electrode arm; and a connecting element which is connected with said electrode arm, said connecting element including a base body, and a sensor selected from the group consisting of a sensor for introducing ultrasound waves into an electrode, a sensor for receiving ultrasound waves, and both, wherein the connecting element is formed as a clamping element which is connectable with the electrode arm so that it fixes the electrode in a clamping seat, wherein outer contours of the clamping element and sensor are formed to correspond with an outer contour of the electrode arm, so that after assembly, the clamping element, the sensor, and the electrode arm together produce a stepless outer contour.

16. A holding device as defined in claim 15; and further comprising a second electrode arm with a second connecting element, formed so that a sensor for introducing ultrasound waves into an electrode is arranged in one of said connecting elements and a sensor for receiving ultrasound waves is arranged in another of said connecting elements.

17. A holding device as defined in claim 15, wherein said electrode arm has a diameter which is greater than a diameter of the electrode, said electrode arm being provided at an end side with an opening for receiving a portion of the electrode.

18. A holding device as defined in claim 15, wherein said electrode arm has a counterplate with which the connecting element is connectable for clamping of the electrode.

19. A holding device as defined in claim 18, wherein said counter plate is formed as a collar-shaped extension of said electrode arm, with which said connecting element is connectable for clamping of the electrode by screw means.

20. A holding device as defined in claim 15, wherein said connecting element has an opening, said sensor being cylinder-shaped and mounted in said opening of said connector element, and also being in contact with an end side of said electrode.

* * * * *